US010188831B2

(12) United States Patent
Elberse et al.

(10) Patent No.: US 10,188,831 B2
(45) Date of Patent: *Jan. 29, 2019

(54) SYSTEMS AND METHODS FOR CATHETER TIP PLACEMENT USING ECG

(71) Applicant: AngioDynamics, Inc., Latham, NY (US)

(72) Inventors: Lambertus Wilhelmus Johannes Elberse, Oss (NL); Franciscus Ludovicus Maria Johannes Veldhuijzen, Liessel (NL)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/232,251

(22) Filed: Aug. 9, 2016

(65) Prior Publication Data

US 2016/0346512 A1    Dec. 1, 2016

Related U.S. Application Data

(63) Continuation-in-part of application No. 14/211,801, filed on Mar. 14, 2014, now Pat. No. 9,445,746.

(Continued)

(51) Int. Cl.
*A61B 5/0402* (2006.01)
*A61B 5/06* (2006.01)
(Continued)

(52) U.S. Cl.
CPC ....... *A61M 25/0133* (2013.01); *A61B 5/0402* (2013.01); *A61B 5/042* (2013.01); *A61B 5/044* (2013.01); *A61B 5/0452* (2013.01); *A61B 5/04525* (2013.01); *A61B 5/061* (2013.01); *A61B 5/065* (2013.01); *A61B 5/06* (2013.01);
(Continued)

(58) Field of Classification Search
CPC ......... A61B 5/042; A61B 5/0456; A61B 5/06; A61B 5/061; A61B 5/04525
See application file for complete search history.

(56) References Cited

U.S. PATENT DOCUMENTS

| 1,989,610 A | 1/1935 | Coolidge |
| 4,249,539 A | 2/1981 | Vilkomerson et al. |

(Continued)

FOREIGN PATENT DOCUMENTS

| AU | 2008329807 | 6/2009 |
| AU | 2010300677 | 4/2012 |

(Continued)

OTHER PUBLICATIONS

Fink, et al, Acustic time-reversal mirrors, IOPscience, 2001, pp. R1-R38.
French, et al, Sensors for Catheter Applications, Wiley-VCH, 2004, pp. 107-153.
Recaldini, et al, Percutaneous Sonographically Guided RF Ablation of Medium Sized Firboids: Feasibility Study, 2007, AJR:189, pp. 1303-1306.

(Continued)

*Primary Examiner* — William J Levicky
(74) *Attorney, Agent, or Firm* — Peter Flora, Esq.

(57) ABSTRACT

A system and method for catheter placement using ECG is provided. In certain embodiments, the system and method can generate a patient specific window for tracking a characteristic of an ECG waveform, such as the amplitude of a P-wave. The patient specific window can be utilized in a system and method for assisting in the placement of a catheter within a patient.

16 Claims, 9 Drawing Sheets

Related U.S. Application Data (60) Provisional application No. 61/782,913, filed on Mar. 14, 2013.

(51) Int. Cl.
  *A61B 5/042* (2006.01)
  *A61M 25/01* (2006.01)
  *A61B 5/0452* (2006.01)
  *A61B 5/044* (2006.01)

(52) U.S. Cl.
  CPC .. *A61B 2505/05* (2013.01); *A61M 2025/0166* (2013.01)

(56) References Cited

U.S. PATENT DOCUMENTS

| | | |
|---|---|---|
| 4,274,423 A | 6/1981 | Mizuno et al. |
| 4,362,166 A | 12/1982 | Furler et al. |
| 4,407,294 A | 10/1983 | Vilkomerson |
| 4,577,634 A | 3/1986 | Gessman |
| 4,644,960 A | 2/1987 | Johans |
| 4,821,731 A | 4/1989 | Martinelli et al. |
| 4,905,698 A | 3/1990 | Strohl, Jr. et al. |
| 4,947,852 A | 8/1990 | Nassi et al. |
| 4,951,677 A | 8/1990 | Crowley et al. |
| 5,038,789 A | 8/1991 | Frazin |
| 5,042,486 A | 8/1991 | Pfeiler et al. |
| 5,078,678 A | 1/1992 | Katims |
| 5,078,714 A | 1/1992 | Katims |
| 5,099,845 A | 3/1992 | Besz et al. |
| 5,121,750 A | 6/1992 | Katims |
| 5,123,419 A | 6/1992 | Platt et al. |
| 5,131,397 A | 7/1992 | Crowley |
| 5,156,157 A | 10/1992 | Valenta, Jr. et al. |
| 5,161,536 A | 11/1992 | Vilkomerson et al. |
| 5,280,786 A | 1/1994 | Wlodarczyk et al. |
| 5,386,828 A | 2/1995 | Owens et al. |
| 5,421,338 A | 6/1995 | Crowley et al. |
| 5,425,367 A | 6/1995 | Shapiro et al. |
| 5,452,359 A | 9/1995 | Inanaga et al. |
| 5,469,858 A | 11/1995 | Osborne |
| 5,500,011 A | 3/1996 | Desai |
| 5,500,100 A | 3/1996 | Riley et al. |
| 5,526,820 A | 6/1996 | Khoury |
| 5,588,436 A | 12/1996 | Narayanan et al. |
| 5,592,939 A | 1/1997 | Martinelli |
| 5,622,169 A | 4/1997 | Golden et al. |
| 5,645,065 A | 7/1997 | Shapiro et al. |
| 5,666,958 A | 9/1997 | Rothenberg et al. |
| 5,709,210 A | 1/1998 | Green et al. |
| 5,727,552 A | 3/1998 | Ryan |
| 5,727,553 A | 3/1998 | Saad |
| 5,729,129 A | 3/1998 | Acker |
| 5,733,323 A | 3/1998 | Buck et al. |
| 5,749,835 A | 5/1998 | Glantz |
| 5,769,786 A | 6/1998 | Wiegel |
| 5,843,076 A | 12/1998 | Webster, Jr. et al. |
| 5,879,297 A | 3/1999 | Haynor et al. |
| 5,899,860 A | 5/1999 | Pfeiffer et al. |
| 5,913,820 A | 6/1999 | Bladen et al. |
| 5,944,023 A | 8/1999 | Johnson et al. |
| 5,954,649 A | 9/1999 | Chia et al. |
| 5,967,980 A | 10/1999 | Ferre et al. |
| 5,983,126 A | 11/1999 | Wittkampf |
| 6,038,468 A | 3/2000 | Rex |
| 6,052,610 A | 4/2000 | Koch |
| 6,061,588 A | 5/2000 | Thornton et al. |
| 6,112,111 A | 8/2000 | Glantz |
| 6,128,958 A | 10/2000 | Cain |
| 6,129,668 A | 10/2000 | Haynor et al. |
| 6,141,293 A | 10/2000 | Amorai-Moriya et al. |
| 6,177,792 B1 | 1/2001 | Govari et al. |
| 6,215,231 B1 | 4/2001 | Newnham et al. |
| 6,216,028 B1 | 4/2001 | Haynor et al. |
| 6,226,546 B1 | 5/2001 | Evans |
| 6,226,547 B1 | 5/2001 | Lockhart et al. |
| 6,230,042 B1 | 5/2001 | Slettenmark |
| 6,233,476 B1 | 5/2001 | Strommer et al. |
| 6,233,477 B1 | 5/2001 | Chia et al. |
| 6,246,231 B1 | 6/2001 | Ashe |
| 6,246,899 B1 | 6/2001 | Chia et al. |
| 6,259,941 B1 | 7/2001 | Chia et al. |
| 6,261,247 B1 | 7/2001 | Ishikawa et al. |
| 6,263,230 B1 | 7/2001 | Haynor et al. |
| 6,298,261 B1 | 10/2001 | Rex |
| 6,304,769 B1 | 10/2001 | Arenson et al. |
| 6,316,934 B1 | 11/2001 | Amorai-Moriya et al. |
| 6,368,285 B1 | 4/2002 | Osadchy et al. |
| 6,374,134 B1 | 4/2002 | Bladen et al. |
| 6,445,943 B1 | 9/2002 | Ferre et al. |
| 6,484,131 B1 | 11/2002 | Amorai-Moriya et al. |
| 6,487,516 B1 | 11/2002 | Amorai-Moriya |
| 6,498,477 B1 | 12/2002 | Govari et al. |
| 6,516,212 B1 | 2/2003 | Bladen et al. |
| 6,522,907 B1 | 2/2003 | Bladen et al. |
| 6,615,155 B2 | 9/2003 | Gilboa |
| 6,618,612 B1 | 9/2003 | Acker et al. |
| 6,625,563 B2 | 9/2003 | Kirsch et al. |
| 6,629,987 B1 | 10/2003 | Gambale et al. |
| 6,636,757 B1 | 10/2003 | Jascob et al. |
| 6,687,531 B1 | 2/2004 | Ferre et al. |
| 6,690,963 B2 | 2/2004 | Ben-Haim et al. |
| 6,695,782 B2 | 2/2004 | Ranucci et al. |
| 6,705,319 B1 | 3/2004 | Wodicka et al. |
| 6,711,429 B1 | 3/2004 | Gilboa et al. |
| 6,738,656 B1 | 5/2004 | Ferre et al. |
| 6,741,883 B2 | 5/2004 | Gildenberg |
| 6,757,557 B1 | 6/2004 | Bladen et al. |
| 6,774,624 B2 | 8/2004 | Anderson et al. |
| 6,892,091 B1 | 5/2005 | Ben-Haim et al. |
| 6,934,575 B2 | 8/2005 | Ferre et al. |
| 6,973,346 B2 | 12/2005 | Hafer et al. |
| 6,977,504 B2 | 12/2005 | Wright et al. |
| 6,980,921 B2 | 12/2005 | Anderson et al. |
| 6,990,427 B2 | 1/2006 | Kirsch et al. |
| 7,015,859 B2 | 3/2006 | Anderson |
| 7,096,148 B2 | 8/2006 | Anderson et al. |
| 7,174,202 B2 | 2/2007 | Bladen et al. |
| 7,197,354 B2 | 3/2007 | Sobe |
| 7,244,234 B2 | 7/2007 | Ridley et al. |
| 7,349,732 B1 | 3/2008 | Kil et al. |
| 7,386,339 B2 | 6/2008 | Strommer et al. |
| 7,575,550 B1 | 8/2009 | Govari |
| 7,580,750 B2 | 8/2009 | Doron et al. |
| 7,606,402 B2 | 10/2009 | Heimdal et al. |
| 7,640,053 B2 | 12/2009 | Verin |
| 7,720,520 B2 | 5/2010 | Willis |
| 7,722,549 B2 | 5/2010 | Nakao |
| 7,782,046 B2 | 8/2010 | Anderson |
| 7,794,407 B2 | 9/2010 | Rothenberg |
| 7,902,817 B2 | 3/2011 | Anderson |
| 7,911,202 B2 | 3/2011 | Anderson |
| 7,914,442 B1 | 3/2011 | Gazdzinski |
| 7,971,341 B2 | 7/2011 | Dukesherer et al. |
| 7,976,518 B2 | 7/2011 | Shaughnessy et al. |
| 7,992,573 B2 | 8/2011 | Wilson et al. |
| 8,167,805 B2 | 5/2012 | Emery et al. |
| 8,180,428 B2 | 5/2012 | Kaiser et al. |
| 8,200,314 B2 | 6/2012 | Bladen et al. |
| 8,226,675 B2 | 7/2012 | Houser et al. |
| 8,228,347 B2 | 7/2012 | Beasley et al. |
| RE43,750 E | 10/2012 | Martinelli et al. |
| 8,280,498 B2 | 10/2012 | Jalde |
| 8,354,827 B2 | 1/2013 | Werle et al. |
| 8,354,837 B2 | 1/2013 | Anderson |
| 8,372,009 B2 | 2/2013 | Emery et al. |
| 8,380,289 B2 | 2/2013 | Zellers et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,432,417 B2 | 4/2013 | Beasley et al. |
| 8,442,618 B2 | 5/2013 | Strommer et al. |
| 8,478,382 B2 | 7/2013 | Burnside et al. |
| 8,512,256 B2 | 8/2013 | Rothenberg |

(56) References Cited

U.S. PATENT DOCUMENTS

| | | | |
|---|---|---|---|
| 8,597,193 B2 | 12/2013 | Grunwald et al. |
| 8,764,728 B2 | 7/2014 | Ciavarella et al. |
| 8,774,907 B2 | 7/2014 | Rothenberg |
| 8,781,555 B2 | 7/2014 | Burnside et al. |
| 8,801,693 B2 | 8/2014 | He et al. |
| 8,849,382 B2 | 9/2014 | Cox et al. |
| 8,858,455 B2 | 10/2014 | Rothenberg |
| 8,864,745 B2 | 10/2014 | Ciavarella et al. |
| 8,937,630 B2 | 1/2015 | Beasley et al. |
| 8,965,490 B2 | 2/2015 | Lee et al. |
| 8,971,994 B2 | 3/2015 | Burnside et al. |
| 9,119,551 B2 | 9/2015 | Qi et al. |
| 9,125,578 B2 | 9/2015 | Grunwald |
| 9,144,431 B2 | 9/2015 | Friedman et al. |
| 9,265,443 B2 | 2/2016 | Rothenberg |
| 9,339,206 B2 | 5/2016 | Grunwald |
| 9,339,207 B2 | 5/2016 | Grunwald et al. |
| 9,345,422 B2 | 5/2016 | Rothenberg |
| 9,415,188 B2 | 8/2016 | He et al. |
| 9,440,047 B1 * | 9/2016 | Elberse ............ A61M 25/0105 |
| 9,445,734 B2 | 9/2016 | Grunwald |
| 9,445,746 B1 * | 9/2016 | Elberse ................ A61B 5/061 |
| 9,456,760 B2 | 10/2016 | Hamatake |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,532,724 B2 | 1/2017 | Grunwald |
| 9,549,685 B2 | 1/2017 | Cox et al. |
| 9,554,716 B2 | 1/2017 | Burnside et al. |
| 9,610,424 B2 | 4/2017 | Ciavarella et al. |
| 9,615,759 B2 | 4/2017 | Hurezan |
| 9,636,031 B2 | 5/2017 | Cox |
| 9,649,048 B2 | 5/2017 | Cox et al. |
| 9,681,823 B2 | 6/2017 | Messerly et al. |
| 9,700,224 B2 | 7/2017 | Ofek et al. |
| 2004/0059237 A1 | 3/2004 | Narayan et al. |
| 2004/0073141 A1 | 4/2004 | Hartley et al. |
| 2004/0097806 A1 | 5/2004 | Hunter et al. |
| 2005/0157888 A1 | 7/2005 | Yang |
| 2006/0025697 A1 | 2/2006 | Kurzweil et al. |
| 2006/0116605 A1 | 6/2006 | Nakao |
| 2006/0173407 A1 | 8/2006 | Shaughnessy et al. |
| 2006/0217655 A1 | 9/2006 | Vitullo et al. |
| 2007/0167738 A1 | 7/2007 | Timinger et al. |
| 2007/0197891 A1 | 8/2007 | Shachar et al. |
| 2007/0197926 A1 | 8/2007 | Danehorn et al. |
| 2007/0213616 A1 | 9/2007 | Anderson et al. |
| 2007/0233185 A1 | 10/2007 | Anderson et al. |
| 2007/0239000 A1 | 10/2007 | Emery et al. |
| 2007/0299353 A1 | 12/2007 | Harlev et al. |
| 2008/0015406 A1 | 1/2008 | Dlugos et al. |
| 2008/0097232 A1 | 4/2008 | Rothenberg |
| 2008/0234711 A1 | 9/2008 | Houser et al. |
| 2008/0249375 A1 | 10/2008 | Obel |
| 2008/0255475 A1 | 10/2008 | Kondrosky et al. |
| 2009/0005675 A1 | 1/2009 | Grunwald et al. |
| 2009/0099468 A1 | 4/2009 | Thiagalingam et al. |
| 2009/0156926 A1 | 6/2009 | Messerly et al. |
| 2009/0177090 A1 | 7/2009 | Grunwald et al. |
| 2009/0203989 A1 | 8/2009 | Burnside et al. |
| 2009/0234328 A1 | 9/2009 | Cox et al. |
| 2009/0259124 A1 | 10/2009 | Rothenberg |
| 2010/0010393 A1 | 1/2010 | Duffy et al. |
| 2010/0036227 A1 | 2/2010 | Cox et al. |
| 2010/0049061 A1 | 2/2010 | Wilson et al. |
| 2010/0152596 A1 | 6/2010 | Griffiths et al. |
| 2010/0204569 A1 | 8/2010 | Burnside et al. |
| 2010/0222664 A1 | 9/2010 | Lemon et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015533 A1 | 1/2011 | Cox et al. |
| 2011/0190712 A1 | 8/2011 | Ciavarella et al. |
| 2011/0196248 A1 | 8/2011 | Grunwald |
| 2011/0201990 A1 | 8/2011 | Franano |
| 2011/0208075 A1 | 8/2011 | Giese et al. |
| 2011/0213260 A1 | 9/2011 | Keel et al. |
| 2011/0230763 A1 | 9/2011 | Emery et al. |
| 2011/0230796 A1 | 9/2011 | Emery et al. |
| 2011/0282188 A1 | 11/2011 | Burnside et al. |
| 2011/0295108 A1 | 12/2011 | Cox et al. |
| 2012/0046562 A1 | 2/2012 | Powers et al. |
| 2012/0059270 A1 | 3/2012 | Grunwald |
| 2012/0095319 A1 | 4/2012 | Kondrosky et al. |
| 2012/0108950 A1 | 5/2012 | He et al. |
| 2012/0109023 A1 | 5/2012 | Emery et al. |
| 2012/0136242 A1 | 5/2012 | Qi et al. |
| 2012/0143029 A1 | 6/2012 | Silverstein et al. |
| 2012/0220854 A1 | 8/2012 | Messerly et al. |
| 2012/0269676 A1 | 10/2012 | Houser et al. |
| 2013/0006102 A1 | 1/2013 | Wilkes et al. |
| 2013/0006229 A1 | 1/2013 | Delaney |
| 2013/0012839 A1 | 1/2013 | Emery et al. |
| 2013/0018248 A1 | 1/2013 | Hurezan |
| 2013/0030413 A1 | 1/2013 | Ciavarella et al. |
| 2013/0060116 A1 | 3/2013 | Messerly et al. |
| 2013/0123597 A1 | 5/2013 | Rothenberg |
| 2013/0217999 A1 | 8/2013 | Burnside et al. |
| 2013/0245434 A1 | 9/2013 | Messerly et al. |
| 2013/0289417 A1 | 10/2013 | Grunwald et al. |
| 2013/0338517 A1 | 12/2013 | Rothenberg |
| 2014/0031674 A1 | 1/2014 | Newman et al. |
| 2014/0046261 A1 | 2/2014 | Newman et al. |
| 2014/0074049 A1 | 3/2014 | Veldhuijzen et al. |
| 2014/0107475 A1 | 4/2014 | Cox et al. |
| 2014/0188133 A1 | 7/2014 | Misener |
| 2014/0243659 A1 | 8/2014 | Rothenberg |
| 2014/0275918 A1 | 9/2014 | Muse et al. |
| 2014/0275922 A1 | 9/2014 | Ciavarella et al. |
| 2014/0296767 A1 | 10/2014 | Franano |
| 2014/0303492 A1 | 10/2014 | Burnside et al. |
| 2014/0309624 A1 | 10/2014 | Bown et al. |
| 2014/0343398 A1 | 11/2014 | He et al. |
| 2015/0018701 A1 | 1/2015 | Cox et al. |
| 2015/0025402 A1 | 1/2015 | Rothenberg |
| 2015/0025465 A1 | 1/2015 | Ciavarella et al. |
| 2015/0080716 A1 | 3/2015 | Powers et al. |
| 2015/0182168 A1 | 7/2015 | Draper et al. |
| 2015/0223775 A1 | 8/2015 | Hamilton, Jr. |
| 2016/0030647 A1 | 2/2016 | Franano |
| 2016/0030648 A1 | 2/2016 | Franano |

FOREIGN PATENT DOCUMENTS

| | | |
|---|---|---|
| CN | 101925333 | 12/2010 |
| CN | 102209490 | 10/2011 |
| CN | 102665541 | 9/2012 |
| CN | 102821679 | 12/2012 |
| CN | 103189009 | 7/2013 |
| CN | 103750858 | 4/2014 |
| EP | 1887940 | 2/2008 |
| EP | 2134402 | 12/2009 |
| EP | 2152150 | 2/2010 |
| EP | 2170162 | 4/2010 |
| EP | 2219526 | 8/2010 |
| EP | 2247234 | 11/2010 |
| EP | 2265175 | 12/2010 |
| EP | 2313143 | 4/2011 |
| EP | 2337491 | 6/2011 |
| EP | 2440122 | 4/2012 |
| EP | 2474268 | 7/2012 |
| EP | 2482719 | 8/2012 |
| EP | 2517622 | 10/2012 |
| EP | 2531098 | 12/2012 |
| EP | 2575611 | 4/2013 |
| EP | 2632360 | 9/2013 |
| EP | 2712547 | 4/2014 |
| ES | 2465915 | 6/2014 |
| JP | 2000131412 | 5/2000 |
| JP | 2011504766 | 2/2011 |
| JP | 5452500 | 3/2014 |
| WO | WO2008129326 | 10/2008 |
| WO | WO2008131017 | 10/2008 |

(56) References Cited

FOREIGN PATENT DOCUMENTS

| | | |
|---|---|---|
| WO | WO2009003138 | 12/2008 |
| WO | WO2009070616 | 6/2009 |
| WO | WO2009120240 | 10/2009 |
| WO | WO2009137262 | 11/2009 |
| WO | WO2010022370 | 2/2010 |
| WO | WO2010030820 | 3/2010 |
| WO | WO2010144922 | 12/2010 |
| WO | WO2011019760 | 2/2011 |
| WO | WO2011041450 | 4/2011 |
| WO | WO2011097312 | 8/2011 |
| WO | WO2012024577 | 2/2012 |
| WO | WO2012040487 | 3/2012 |
| WO | WO2012058461 | 5/2012 |
| WO | WO2012064769 | 5/2012 |
| WO | WO2012068365 | 5/2012 |

OTHER PUBLICATIONS

Mohammad, et al, A Signal and symptoms of object oriented programming approach to development of ECG Analysis Software, Computers in Cardiology 2002, pp. 153-156.

Rangayyan, Analysis of Concurrent, Coupled, and Corrolated Processes, Institute of Electrical Engineers 2002, pp. 51-71.

Jenkins, et al, Computer Diagnosis of Abnormal Cardiac Rhythms Employing a New P-Wave Detector for Internal Movement, Computers and Biomedical Research 1978, pp. 17-33.

Jenkins, et al, Computer Diagnosis of Supraventricular and Ventricular Arrhythmias, Circulation, 1979, pp. 977-987.

Dilaveris, et al, P-Wave Dispersion: A Novel Predictor of Proxysmal Atrial Fibrillation, ANA 2001, pp. 159-165.

Feld, et al, RF Catheter Ablation for the treatment of Human Type 1 Atrial Flutter, Circulation, 1992, pp. 1233-1240.

* cited by examiner

SYSTEMS AND METHODS FOR CATHETER TIP PLACEMENT USING ECG

CROSS-REFERENCE TO RELATED APPLICATIONS

This application claims priority to U.S. Provisional Application No. 61/782,913, filed on Mar. 14, 2013 and titled Method for Locating a Catheter Using Intracardial ECG; and U.S. Nonprovisional application Ser. No. 14/211,801, filed Mar. 14, 2014, entitled SYSTEMS AND METHODS FOR CATHETER TIP PLACEMENT USING ECG, both of which are incorporated herein by reference in their entireties.

FIELD OF THE INVENTION

The present invention relates generally to positioning a catheter tip within a human body. More specifically, the invention relates to systems and methods that utilize ECG for assisting with catheter tip placement procedures.

BACKGROUND OF THE INVENTION

Medical professionals commonly use catheters for gaining prolonged access to an area within the body. Once the catheter tip is positioned at the target location, treatments such as antibiotics, chemotherapy, pain medicine, and nutrition can be administered. If the catheter tip is improperly positioned during insertion, various risks to the patient arise, including a fluid infusion that causes pain or injury to the patient, complications due to increased thrombosis rates, delays in therapy, catheter malfunction and additional costs.

General standards for proper catheter insertion depend on the type of catheter and the treatment being provided. For example, peripherally inserted central catheters (or PICC lines) are commonly inserted into a brachial, cephalic or basilic vein in the arm and advanced through the venous system towards the superior vena cava (SVC). Current medical standards recommend that the distal tip of the catheter terminate in the lower ⅓ of the SVC, close to the junction of the SVC and the right atrium (RA). However, since PICCs are commonly inserted into a vein in the arm and advanced through the venous system to reach the SVC, the PICC line tip may be inadvertently positioned in a non-target area, such as the internal jugular, the subclavian vein, or too far past the SVC-RA junction and into the heart.

Catheter tip location techniques have improved the ability of medical professionals to verify the location of the catheter tip. One technique uses fluoroscopy to confirm tip location. Fluoroscopy provides the operator with real-time images of the patient's anatomy using a fluoroscope. Another technique uses a combination of an electromagnetic beacon and an electromagnetic detection element to track the beacon positioned near the catheter tip. Many techniques have also been described for using electrocardiography (ECG) to assist with catheter tip placement by measuring an ECG signal from an intravascular (IV) electrode positioned at or near the catheter tip.

Tracking ECG waveform changes measured from an IV electrode as the catheter advances through the vasculature towards the SA node can provide valuable feedback to the medical professional placing the catheter, since the SA node is located near the SVC-RA junction. Specifically, tracking the P-wave morphology is known to be a valuable tool. For example, as the IV electrode advances down the SVC towards the SA node, the amplitude of the P-wave will start to rise. The amplitude of the P-wave will eventually peak when the IV electrode is closest to the SA node, and eventually start to decrease in amplitude as the IV electrode moves away from the SA node and enters the RA. Observation of this phenomenon has been utilized by medical professionals for catheter placement procedures at least as early as the mid-$20^{th}$ century.

Automated systems that track P-wave morphology for catheter tip placement have also been previously described. For example, in U.S. Pat. No. 5,121,750 to Katims, incorporated herein by reference, a monitoring system detects changes in the P-wave as measured from an IV electrode for providing automated user instructions on catheter placement. The monitoring system (1) detects increases in the P-wave amplitude as the IV electrode approaches the SA node and signals the user to continue advancing the catheter, (2) detects a decrease in the P-wave amplitude as the IV electrode passes the SA node and signals the user to pull back the catheter, and (3) detects that the P-wave is within a certain range of the maximum and signals the user to stop once within that range.

For tip positioning systems that rely on tracking changes in P-wave amplitude for providing user feedback, several obstacles may arise. For instance, P-wave location and morphology can change from patient to patient based on a number of factors (explained in further detail below). It would be beneficial for an ECG and P-wave based tip location system to have a more patient specific analysis approach to account for patient-to-patient variability. Further, ECG signals from IV electrodes tend to have low resolution due to a number of factors, including electrode downsizing and design limitations, movement, and pickup of physiologic and extraphysiologic artifacts. A noise spike may cause the algorithm to misinterpret the acquired signal, possibly leading to erroneous user feedback. Systems that can accurately provide user feedback, manage lower resolution IV electrode signals, and minimize the influence of ECG artifacts on signal processing would be advantageous.

Further, problems such as thrombus buildup at the catheter tip and within the catheter lumen can affect IV ECG signal acquisition. Thrombus buildup can partially block electrode exposure which can result in a muted signal. Further, thrombus buildup in contact or near the electrode can cause the IV ECG signal to refract off of the thrombus formations, adding noise to the IV ECG waveform. To clear the catheter lumen and opening of thrombus, and to combat the formation of new thrombus, the catheter lumen can be flushed with saline. However, this can add time and cost to the procedure. Further, prolonged interruptions in catheter advancement may interfere with the normal execution of the tip location algorithm, and may prevent the algorithm from properly executing, or lead to erroneous user feedback.

Improved catheter tip placement systems and methods for overcoming these issues is desired.

SUMMARY OF THE INVENTION

The invention is directed to a system and method for catheter tip placement using ECG. In one aspect, the invention is a system and method for establishing an ECG search window for catheter tip placement. In another aspect, the invention is a system and method for assisting in the placement of a catheter within a patient. In yet another aspect, the invention is a system and method for high clarity signal acquisition in tip location systems utilizing an intravascular electrode. In certain aspects, a method for establishing an ECG search window for a catheter tip placement system includes the steps of acquiring multiple surface ECG signals from at least one surface ECG electrode; generating a signal averaged surface ECG signal from the multiple surface ECG signals; determining a first fiducial point by identifying an extremum within the signal averaged surface ECG signal; establishing a first ECG search window between first and second predetermined values offset from the first fiducial point; determining a second fiducial point by identifying an extremum in the first ECG search window; determining a search window beginning value by identifying a local extremum on a first side of the second fiducial point, and determining a search window ending value by identifying a local extremum on a second side of the second fiducial point; and establishing a second ECG search window between the search window beginning value and the search window ending value so that the second ECG search window is narrower than the first ECG search window.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIGS. 3A-3F are exemplary P-wave morphologies.

FIGS. 4A-4C are diagrams of a human body illustrating various surface electrode configurations according to exemplary embodiments of the invention; FIG. 4A illustrates a 3 surface electrode configuration; FIG. 4B illustrates a 4 surface electrode configuration.

FIGS. 8A-8D show a tip location user feedback graphical user interface (GUI) according to an exemplary embodiment of the invention.

DETAILED DESCRIPTION OF THE INVENTION

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting. Systems and methods described below are compatible with ECG assisted placement for a variety of medical devices, including for example PICCs, central venous catheters, midline catheters, port catheters, and dialysis catheters.

Referring now in detail to the drawings, in which like reference numerals indicate like parts or elements throughout the several views, in various embodiments, presented herein are systems and methods for catheter tip placement using ECG.

Figure 1:
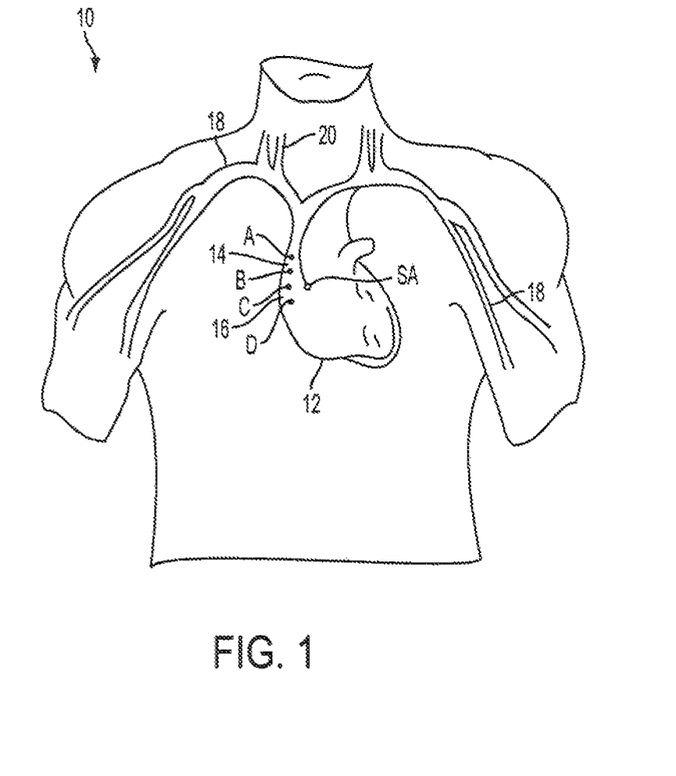
FIG. 1 is a diagram of an upper portion of a human body illustrating various positions of the vasculature, including the SVC, RA and SA node.

As described above, catheters such as PICC lines are commonly inserted into a brachial, cephalic or basilic vein in the arm and advanced through the venous system towards the SVC-RA junction with the goal of having the catheter tip terminate in the lower ⅓ of the SVC. As shown in FIG. 1, a human body 10 has a vasculature system 18 leading to the heart 12. Using P-waves as a guidance measure and the SA node (SA) as a reference point, an IV electrode located near a PICC tip can track changes in the P-wave generated from the SA node (SA) as the PICC tip and IV electrode advance towards the SVC 14 and the RA 16. As described in Katims, an algorithm can be employed to detect increases in P-wave amplitude as the IV electrode advances from positions A to B, and then B to C. When the IV electrode passes the SA node (SA) and moves from position C to D, the algorithm detects a decrease in P-wave amplitude and a user command can be given indicating that the PICC be pulled back until either the maximum P-wave is reached again, or until a percentage of the maximum P-wave is detected. If, for example, the algorithm detects a severe and premature drop in P-wave amplitude during insertion, or if the P-wave never meets an incrementing threshold, that could indicate that the PICC tip accidently migrated up to the internal jugular 20 instead of down towards the SVC 14.

Figure 2:
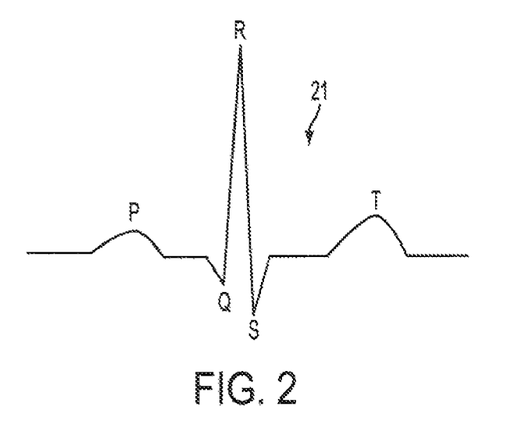
FIG. 2 is an exemplary ECG waveform showing typical shapes and positions of common ECG waves.

For tip location systems that rely on an algorithm to interpret changes in P-waves, the ability of the system to accurately identify the P-wave given patient-to-patient P-wave variability and noise are important to system reliability and accuracy. As shown in FIG. 2, the P-wave is not typically the most prominent wave in an ECG waveform. The QRS complex is typically the most prominent waveform and is therefore considered the simplest to detect, primarily because of the sharp delineation of the R-wave. Other waves, such as the T-wave or the U-wave (not shown) may also present as prominent or diminished depending on various factors.

Figure 3A:
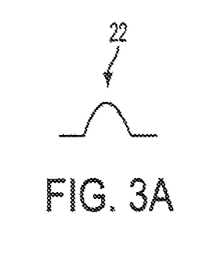
FIG. 3A shows a normal P-wave.
Figure 3B:
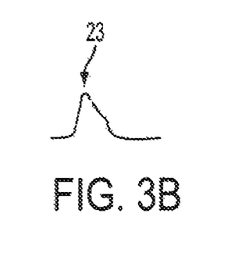
FIG. 3B shows a P-wave with a higher initial positive deflection.

Patient variability in P-wave morphology is not uncommon. FIGS. 3A-3F illustrate just a few common examples of P-wave morphologies. A normal P-wave is illustrated in FIG. 3A. A normal P-wave 22 is formed in part by the combination of right and left atrial depolarization waves in sequence. The P-wave 23 illustrated in FIG. 3B shows a higher initial positive deflection, which could be caused by right atrial enlargement, leading to a more pronounced peak during right atrial depolarization. Right atrial enlargement is common in patients suffering from pulmonary hypertension.

Figure 3C:
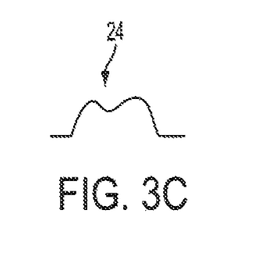
FIG. 3C shows a P-wave with a notch near the peak.
Figure 3D:
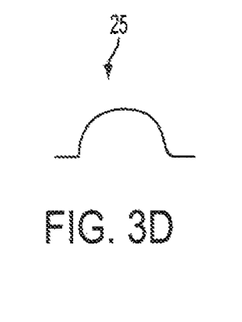
FIG. 3D shows a prolonged P-wave.
Figure 3E:
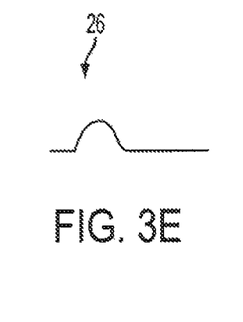
FIG. 3E shows an offset P-wave.

Left atrial enlargement could cause a P-wave 24 with a notch near the peak as shown in FIG. 3C, or a prolonged P-wave 25 as shown in FIG. 3D. P mitrale or a notched P-wave may also be due to mitral stenosis. An offset P-wave 26 as shown in FIG. 3E could result in patients having atrial fibrillation or extrasystoles. Numerous other factors including respiratory rate, heart rate, prior surgeries (e.g. a MAZE procedure), or patient conditions (e.g. ventricular tachycardia, Wolff-Parkinson-White syndrome or atrial disease) could impact P-wave morphology and patient variability.

Figure 3F:
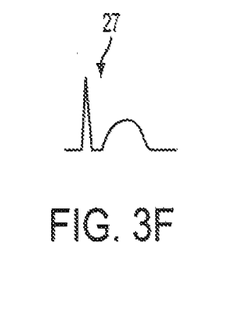
FIG. 3F shows a spike artifact followed by a normal P-wave.

Even if a patient presents a normal P-wave, an artifact such as the spike artifact shown in the P-wave 27 of FIG. 3F could appear near or on top of the P-wave, leading to a misinterpretation of the P-wave amplitude during signal processing. In general, artifacts can be generated from physiologic or extraphysiologic sources, such as patient movement, electrical noise from other parts of the body, and interference from medical equipment and other sources of electrical disturbance in the local environment. Systems and methods according to the present invention improve P-wave and ECG based tip location systems as described further below.

Figure 4A:
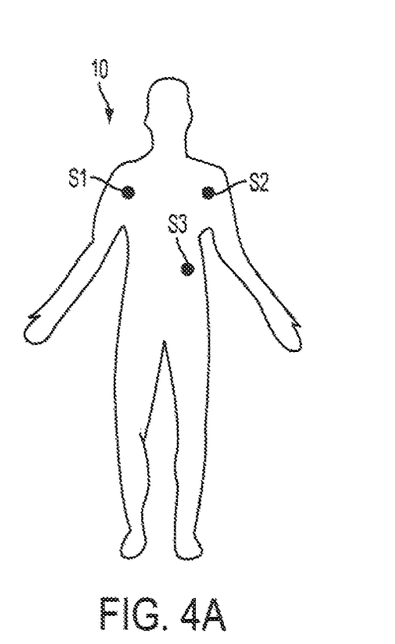
Figure 4B:
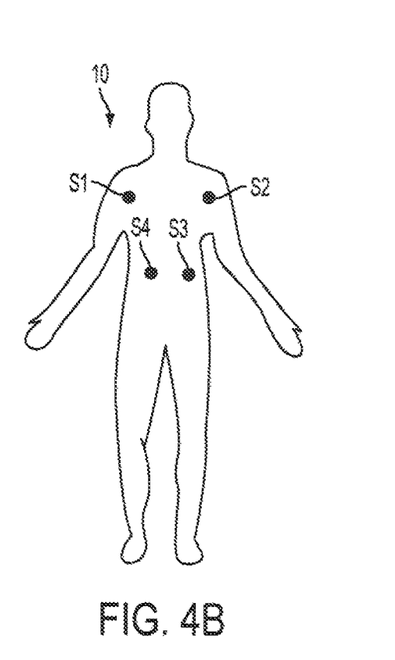

According to an embodiment of the invention, multiple surface electrodes and a single IV electrode are utilized for ECG signal acquisition. Alternative embodiments may utilize a single surface electrode or multiple IV electrodes. In this exemplary embodiment and as illustrated in FIG. 4A, three surface electrodes S1, S2, S3 are placed on a surface on the skin of the patient 10 to acquire a surface ECG waveform. This configuration, utilizes an right arm (RA—white) lead S1, a left arm (LA—black) lead S2, and a left leg (LL—red) lead to form what is commonly referred to as Einthoven's Triangle. In an alternative embodiment, an additional neutral lead (N) S4 can be positioned as a right leg lead S4, as shown in FIG. 4B. An IV electrode IV1 will also be utilized by the system for acquiring an IV ECG signal as the IV electrode is advanced through the vasculature.

Figure 4C:
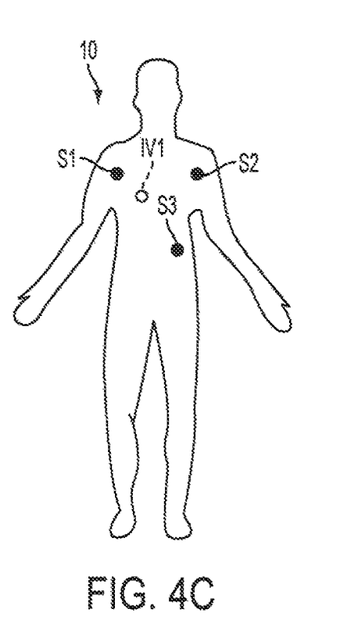
FIG. 4C illustrates a 3 surface electrode configuration with an IV electrode.
Figure 5:
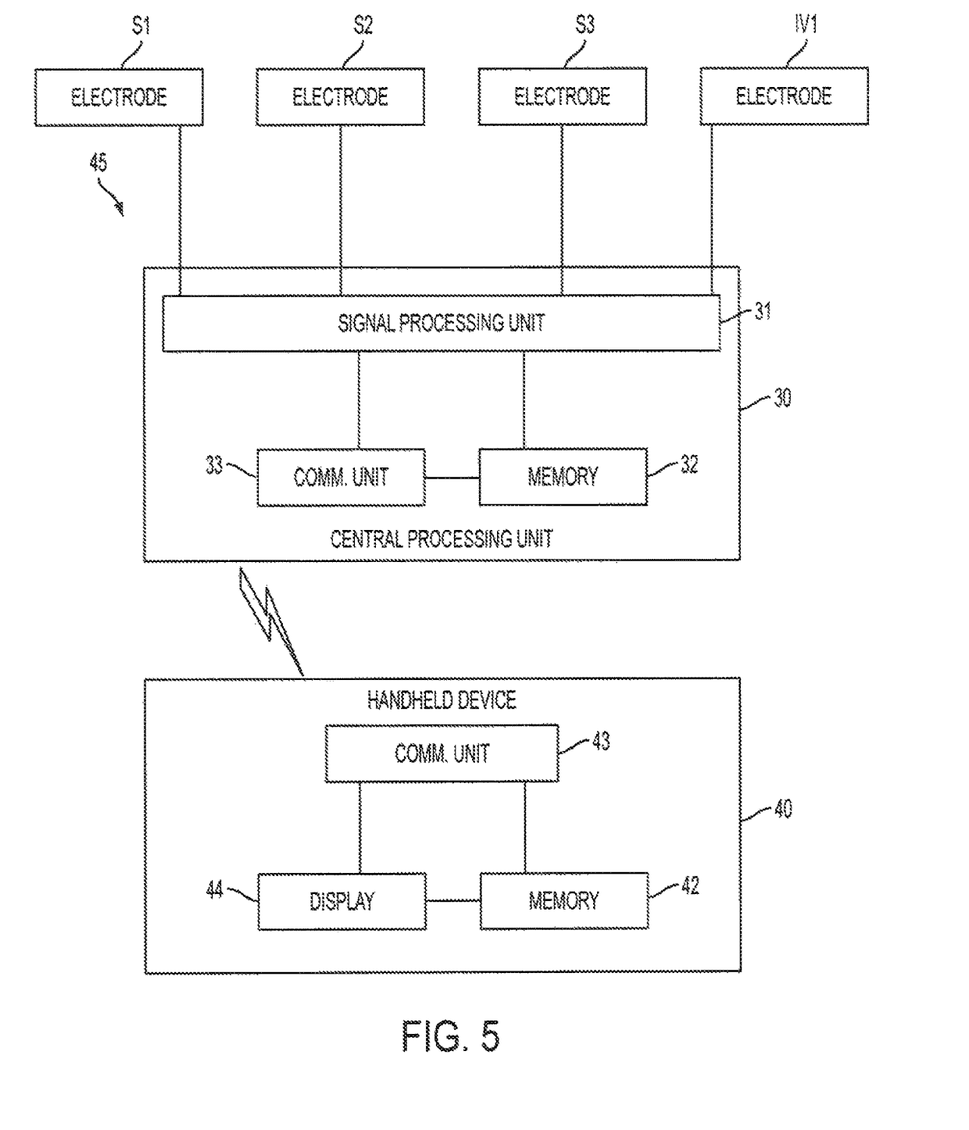
FIG. 5 is a diagram of a catheter tip placement system according to an exemplary embodiment of the invention.

As shown in the system diagram of FIG. 5 (and using the example configuration shown in FIG. 4C), all of the electrodes S1, S2, S3, IV1 are operably connected to a central processing unit 30 of the tip location system 45. The three surface ECG electrodes S1, S2, S3, and the IV electrode IV1 connect to a signal processing unit 31, where the signals are acquired and processed by the tip location algorithm. A memory unit 32 can be used to store data including waveforms, algorithm variables and error messages. The communication unit 33 on the central processing unit 30 can transmit data via a hardwired or wireless connection to a communication unit 43 on a handheld device. The handheld device 40 can be for example a smart phone or a table. Alternatively, this device 40 can be a unit mounted on a pole or otherwise stationary in the medical suite. A display 44 such as a touch-screen display can be integral to the handheld device, which communicates with the communication unit 43 and a memory unit 42. The display can communicate user feedback to the medical professional performing the procedure, such as catheter advancement instructions, ECG waveforms and error messages. A touch-screen on the display can be used to communicate information between the medical professional and the tip location system 45. In alternative embodiments, the central processing unit 30 and the handheld device 45 are a single integral unit forming the tip location system 45.

A customized and patient specific IV ECG search window can be established under the following method according to an exemplary embodiment of the invention. For signal acquisition, the patient is prepped with an electrode configuration as illustrated in FIG. 4C. Now, with reference to FIG. 6, a surface ECG waveform 35 is acquired from surface ECG electrodes. The surface ECG waveform 35 can represent a single heartbeat cycle as measured directly from one ECG electrode, a waveform that has been averaged among measurements from multiple surface ECG electrodes (e.g. Wilson's central terminal), a signal averaged waveform from one or more surface ECG electrodes averaged over multiple heartbeats, a waveform run through a filter, or a combination of the above to increase the waveform resolution. In a preferred embodiment, the surface ECG waveform 35 is a signal averaged waveform, averaged from multiple surface ECG electrodes and further averaged over 10-20 heartbeats. Once the signal averaged surface ECG waveform 35 has been generated, it is analyzed to find the peak of the R-wave 50 as an initial fiducial point. A number of R-wave or QRS detection algorithms known in the art can be incorporated for this purpose, including Pan Tomkins, Hilbert transformation, wavelet coefficient estimation, linear filtering and model based approaches. Alternative fiducial points such as the onset or offset of the R-wave, the Q-wave or the S-wave can also be used.

Figure 6:
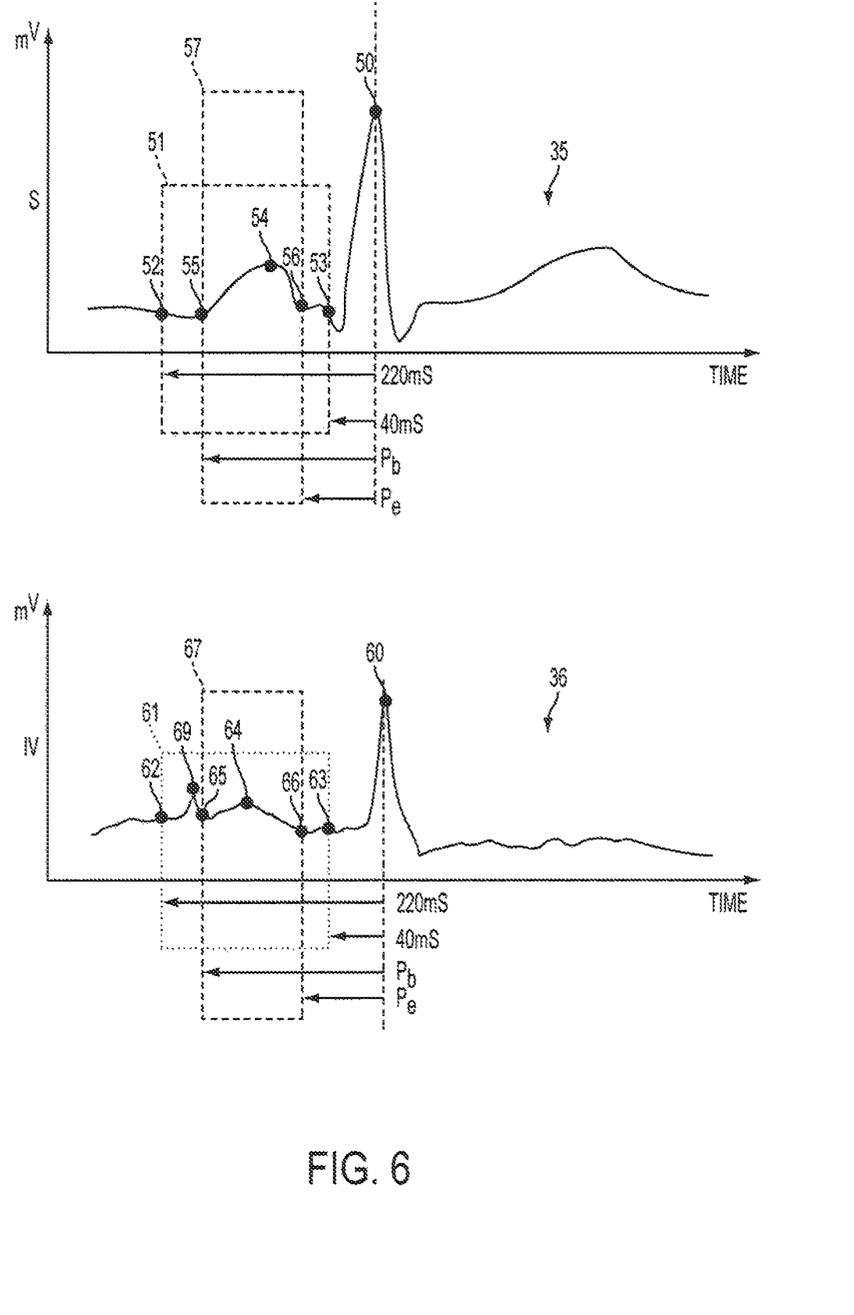
FIG. 6 is a set of waveforms diagram showing a search window generated according to a surface ECG waveform and overlaid onto an IV ECG waveform according to an exemplary embodiment of the invention.

After the peak of the R-wave 50 is identified, an initial P-wave search window 51 is established based on a generalized area of where the P-wave can be expected to appear in all patients, accounting for P-wave variability between patients. In this embodiment, two predetermined points, 220 ms (52) prior to the R-wave peak 50 and 40 ms (53) prior to the R-wave peak 50 form the beginning and ending of the initial P-wave search window 51. Other predetermined points, which may range for example between 20-60 ms and 200-240 ms can be used. With the initial P-wave search window 51 now established, the peak of the P-wave 54 is identified as the absolute peak within the initial P-wave search window 51. Isolated noise, interference, and aberrant spikes will be filtered out of the surface ECG waveform 35 during the signal averaging step, minimizing the possibility that they will falsely present as the absolute peak within the initial P-wave search window 51.

Using the peak of the P-wave 54 as a second fiducial point, the first local minima to the left 55 and right 56 sides of the peak of the P-wave 54 are identified to form the bounds of a patient specific surface ECG P-wave window 57. A first variable Pb represents the beginning of the surface ECG P-wave window 57 based on the distance between the minimum to the left side 55 of the peak of the P-wave 54 and the R-wave 50. A second variable Pe represents the end of the surface ECG P-wave window 57 based on the distance between the minimum to the right side 56 of the peak of the P-wave 54 and the R-wave 50. In alternative embodiments, it could be advantageous to expand one or more edges of the patient-specific P-wave window to a subsequent second or third local minimum. For example, the system might initially identify a notch in the P-wave (see for example FIG. 3C) as the first local minimum (to the left or right of the P-wave peak). In this case, sensing that the first left or right local minimum is in too close in proximity (in amplitude or time) to the P-wave peak, the system may recognize a false edge of the P-wave and expand the window to a subsequent local minimum, generating a more relevant P-wave window for that particular patient. In yet another alternative embodiment, edges of the patient specific P-wave window can be established based on a predetermined distance surrounding the P-wave peak. Further, patient specific P-wave window edges can be further expanded or narrowed to deal with a number of factors, including P-wave morphology or noise in signal. Other windows described herein can be further modified in a similar fashion.

Once the patient specific surface ECG P-wave window 57 is established using the surface ECG waveform 35, it can be overlaid onto the IV ECG waveform 36 to form a patient specific IV P-wave search window 67. To generate the IV P-wave search window 67, the R-wave 60 in the IV ECG waveform 36 is first identified using a QRS complex or R-wave detection technique. Then, Pb and Pe, determined from analysis of the surface ECG, are offset to the left of the R-wave 60, establishing the beginning 65 and ending 66 of the IV P-wave search window 67. This technique allows the system to establish a patient specific IV P-wave search window using the higher resolution surface ECG waveform, then transfer the surface ECG P-wave search window to the lower resolution IV ECG signal for more accurate signal processing during the catheter placement procedure. If, in this example, a generic non patient specific search window 61 was applied to the IV ECG waveform 36 with non patient specific beginning 62 and ending 63 points, an artifact spike 69 would have presented as the local maximum, throwing off the tip location algorithm which relies on tracking the P-wave amplitude 64. Using this method, the only wave in the lower resolution IV ECG waveform 36 that needs to be specifically identified is the R-wave 60, which is sharply delineated even in lower resolution ECG waveforms. This improved tip location ECG signal processing technique allows for consistent identification of the P-wave in the lower resolution IV ECG waveform, and provides a technique that is efficient enough to run in real time for live user feedback during the catheter placement procedure.

It is important to note that the ECG waveform may appear as inverted depending on a number of factors affecting waveform polarity, including for example ECG lead configuration, whether or not the signal acquisition equipment is set to invert acquired signals, and physical abnormalities changing normal electrophysiological conduction paths. Thus, for example, if the surface ECG waveform 36 shown in FIG. 6 was inverted, the R-wave peak 50 and the P-wave peak 54 would present as minimums instead of maximums. The method described above for customizing a patient specific IV ECG search window can be adjusted to detect waveforms presenting as either local minimums or local maximums since either type of extremum can just as easily be located and tracked. Adjustments for changing the type of extremum being tracked can happen automatically using a simple test algorithm such as a peak detection or baseline analysis algorithm. Alternatively, the system can measure absolute values of extrema so that the displacement of the deflection, and not the positive or negative value of the deflection becomes the relevant measure.

Figure 7A:
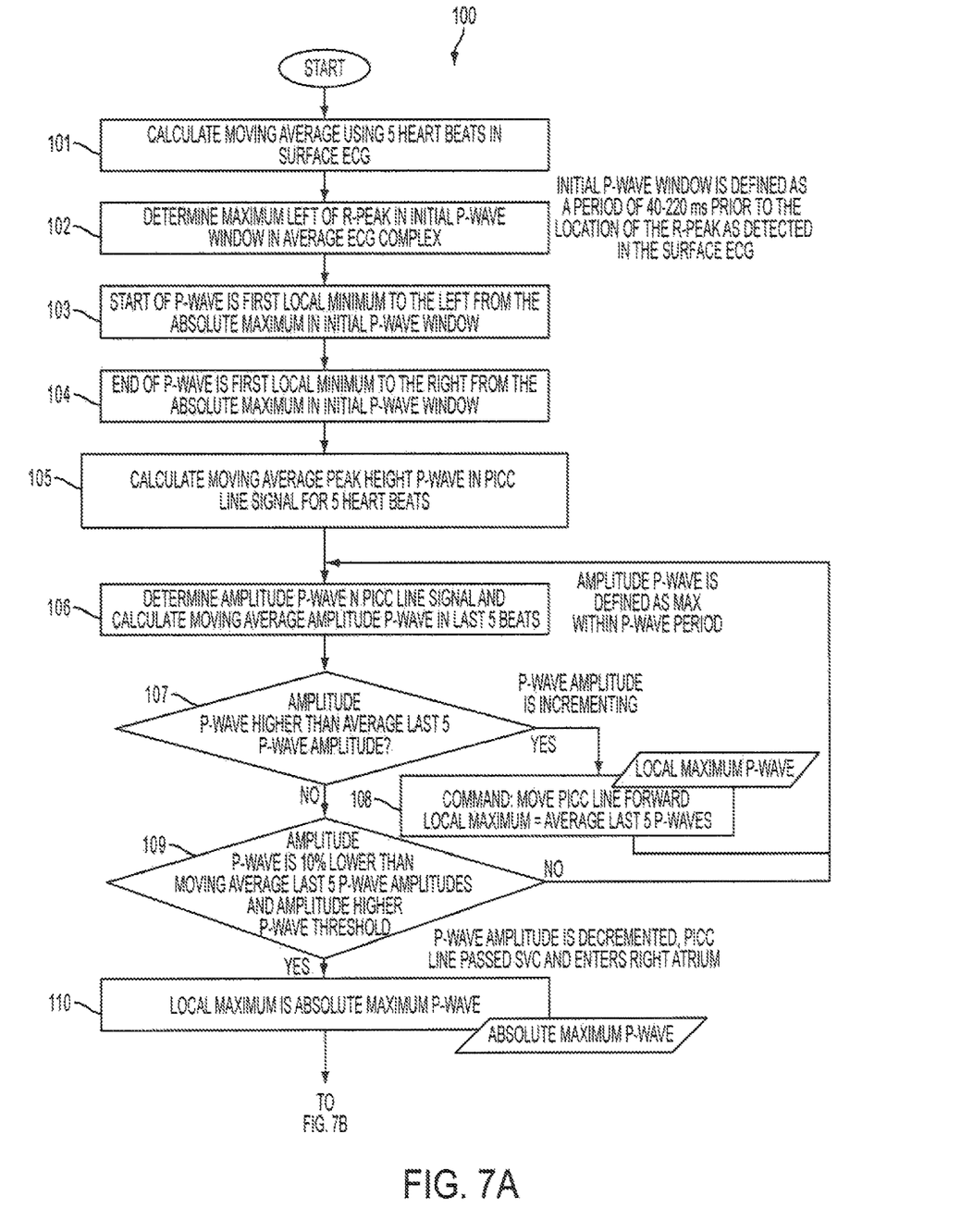
FIGS. 7A and 7B show a flow chart for a tip location algorithm according to an exemplary embodiment of the invention.
Figure 7B:
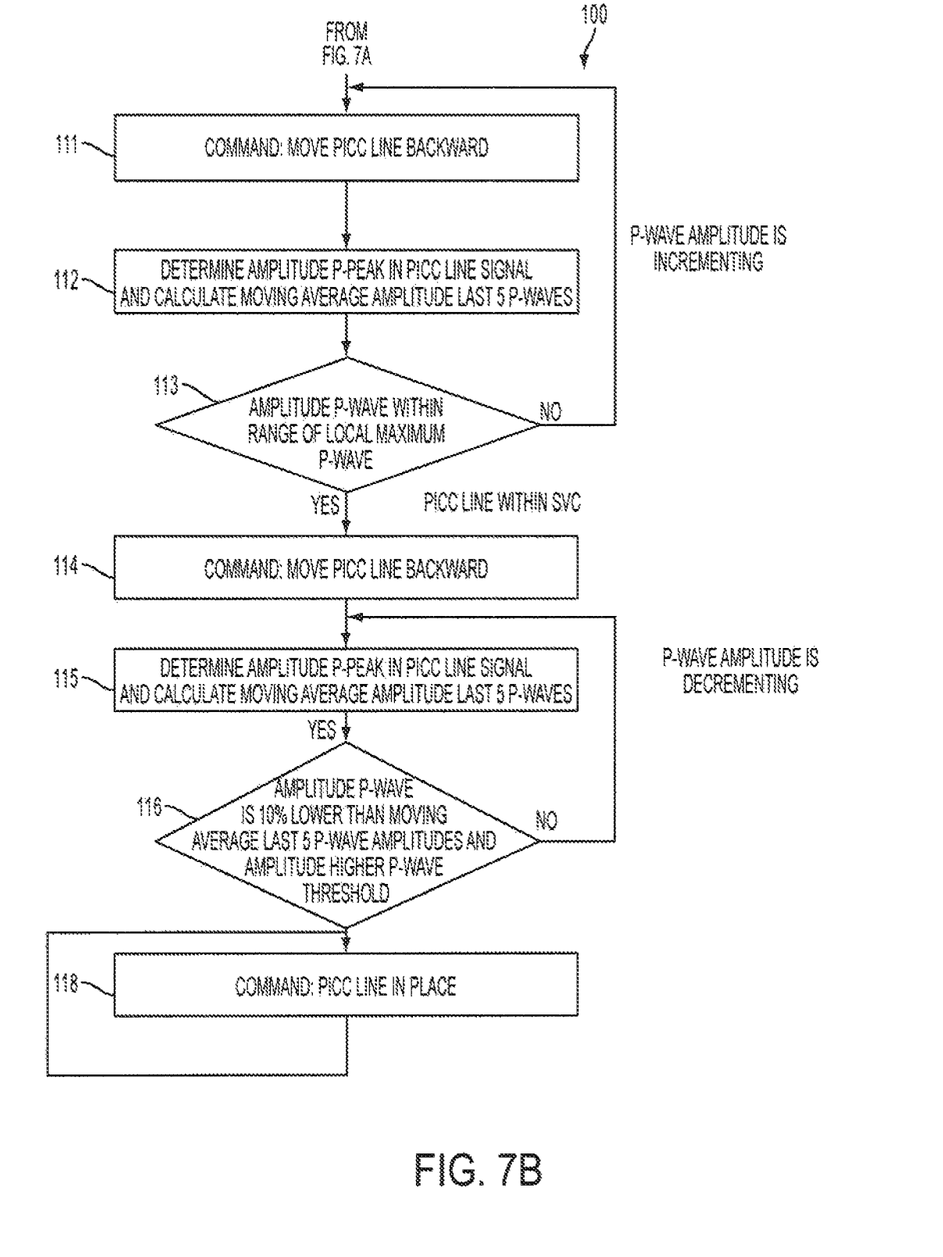
Figure 8A:
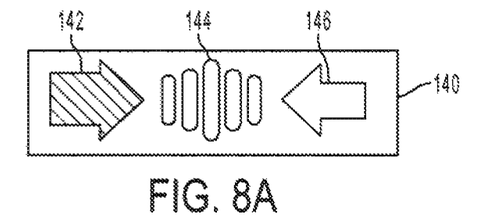
FIG. 8A is a graphical view of a GUI command to move forward.
Figure 8B:
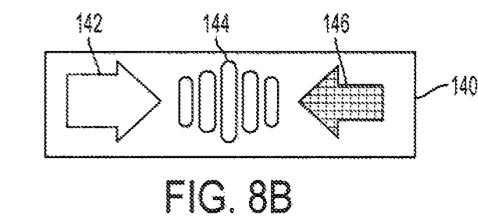
FIG. 8B is a graphical view of a GUI command to move backward.
Figure 8C:
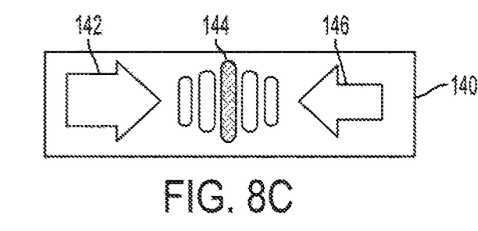
FIG. 8C is a graphical view of a level indicator GUI command to stop.
Figure 8D:
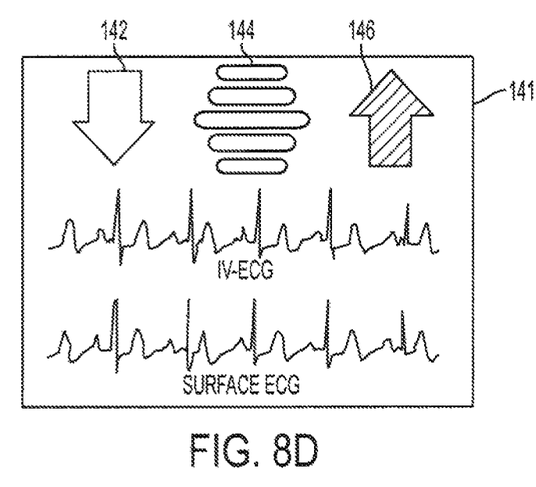
FIG. 8D is a graphical view of a GUI including user commands, IV ECG waveforms and surface ECG waveforms.

An algorithm for placing a PICC line according to an exemplary embodiment of the invention is now explained with reference to the flow chart 100 shown in FIGS. 7A and 7B. First, with reference to FIG. 7A, a surface P-wave window is established in similar fashion to the method described above. ECG signals are acquired from surface ECG electrodes to create a signal averaged surface ECG signal 101, and the QRS complex is identified. The initial window for finding the P-wave is determined by looking to the left of the R-peak at the period between 40-220 ms prior to the R-wave peak 102. The peak of the P-wave is identified by finding the absolute maximum of the signal averaged surface ECG in the initial P-wave window. To find a beginning value for a patient specific P-wave window, the algorithm first looks at the surface ECG signal left of the P-wave peak and identifies the first local minimum 103.

Similarly, to find an ending value for the patient specific P-wave window, the first local minimum right of the P-wave peak is identified 104. The identified left and right local minimums provide the beginning and ending values for a patient specific window that can now be applied to P-wave analysis in the IV ECG signal as explained above with reference to FIG. 6. The moving average peak height of the P-wave in the PICC line signal is then calculated for 5 heart beats 105.

The term "moving average" used herein may be defined as averaging the most current ECG wave recording together with previous ECG wave recordings. The system described herein will include the oldest recorded individual ECG wave being continuously and automatically rolled out or replaced in the calculation by the newest or most recent individual ECG wave recorded. Therefore, the system may be comprised of multiple moving average sets, with each moving average set being comprised of a specific number of the most recent individual ECG wave recordings. It is within the conception of this invention that the specific number of individual ECG wave recordings in a moving average set may vary, since the number of individual ECG waves included in a moving average set may impact the clarity of the PICC location. For purposes of PICC location of this system it has been found that using up to five individual ECG wave recordings per moving average set provides adequate data for proper PICC location results.

An example of using the moving average in this system may include creating a first moving average set by storing the first five ECG waves recorded during the procedure: "1→2→3→4→5". Within this first moving average set "1" represents the first or earliest ECG wave detected while "5" represents the most recent or latest ECG wave detected. The second moving average set may comprise the next ECG wave "6" detected and automatically replaces the oldest or first ECG wave "1" in the moving average calculation: "2→3→4→5→6". The third moving average set may comprise the next ECG wave "7" detected and automatically replaces the oldest remaining ECG wave "2" in the moving average calculation: 3→4→5→6→7. It is within the conception of this invention that multiple moving average sets may be used during a single PICC placement procedure, with each moving average set automatically replacing the oldest ECG wave in chronological order with the most recent ECG wave recorded.

An advantage of using a moving average is to improve accuracy of the IV ECG wave interpretation. The accuracy of the IV ECG signal is critical to this invention because the IV ECG signal is constantly changing as the catheter is advanced or retracted. The surface ECG signal is then used to clarify and filter the IV ECG signal. It was found that measuring the signals of at least five ECG waves sufficiently improved the accuracy of the IV ECG wave interpretation. When less than five ECG waves are used there is a risk that the average may be skewed in cases of arrhythmias Next, a series of steps for providing user instruction during the PICC placement procedure are executed based on P-waves acquired from the IV ECG electrode located at or near the tip of the PICC. The algorithm determines the amplitude P-wave in the PICC line signal and then calculates the moving average amplitude P-wave in the last 5 heart beats 106. A decision is made based on how the IV ECG P-wave amplitude changes 107. If the P-wave amplitude is higher than the average of the most previous five P-wave amplitudes, then that indicates that the P-wave is incrementing, and the user is told to advance the PICC forward 108. A "local maximum P-wave" value is calculated and saved in memory as the average of the last five P-waves, and the algorithm loops back to determine again whether or not the current P-wave amplitude is higher than the average of the most previous five P-wave amplitudes. The user command to advance will typically be repeated for multiple cycles, as the IV electrode approaches the SA node. Alternatively, if a current P-wave amplitude is lower than the average of the most previous five P-wave amplitudes, a further decision is made as to whether or not the amplitude of the P-wave 10% lower than the moving average of the last five p-wave amplitudes, and whether or not the amplitude of the P-wave is higher than the P-wave threshold 109. The 10% threshold is for determining if the drop in the P-wave was significant, indicating that the SA node may have been passed. However, a second check against the P-wave threshold value is to ensure that the drop in the P-wave is at the very least above the P-wave threshold amplitude recorded when the IV electrode was positioned much further away from the SA node at the beginning of the procedure. If both the amplitude of the P-wave is at least 10% lower than the moving average of the last five p-wave amplitudes and higher than the P-wave threshold, the algorithm determines that the absolute maximum P-wave has been reached. The most recent "local maximum P-wave" value becomes the "absolute maximum P-wave" value, and is saved in memory 110. At this point, user feedback instructs the user to move the PICC line backwards 111, and the amplitude of the P-wave is measured and the moving average of the five most recent P-waves are calculated 112.

The next series of steps determines user feedback for moving the PICC line and IV electrode backwards to the target site. First, the algorithm instructs the user to pull back the PICC line until the averaged P-wave amplitude is within a particular range of the "local maximum P-wave" amplitude 113. An incrementing P-wave is now being tracked. When the P-wave amplitude is within range, the user is instructed to continue to move the PICC line backwards 114. The amplitude of the P-wave continues to be measured and the moving average of the five most recent P-waves is calculated 115. A decreasing P-wave amplitude is now tracked, and a decision is made regarding whether or not the average amplitude enters the range of 10% lower than the moving average of the last five p-wave amplitudes 116. If the average amplitude is within the 10% or lower range, the user is notified that the PICC tip is at the target location 118. If not, the algorithm loops back to tracking the decrease in averaged P-wave amplitude. If the user pulls back too far, the algorithm can automatically loop back to an earlier advance state, or a restart feature can return the algorithm back to the beginning. In addition, the system can be modified so that the center bar reflects particular ranges that correspond with the type of procedure being performed or the type of catheter being placed. So for example, if the target location for the catheter tip is further up the SVC, the center bar may be set to a 65-75% range. Alternatively, if the target location for the catheter tip is further down into the RA, the algorithm can be modified so that the user is instructed to stop once the decrementing P-wave amplitude reaches a particular range after hitting the maximum P-wave.

Now with reference to FIGS. 8A-8D, examples of GUIs 140, 141 for user feedback are shown. Graphical instructions such as arrows, words, colors, or other symbols indicating advance PICC 142 or pull back PICC 146 could signal an instruction to the user. Alternatively or concurrently, audio commands can be utilized. The GUI 140, 141 could be part of a touch screen handheld device, such as a smart phone or a tablet. A GUI showing level indicators 144 can also be included. Waveforms of the surface ECG and IV ECG signals can also run on the screen so that the user can monitor the resolution of the signal and the ECG status of the patient.

In certain embodiments, a tip location procedure record is generated after each procedure for the patient's record. The tip location procedure record could record information including: (1) patient background information, including name, date of birth, a patient ID number, a catheter description, a user ID and miscellaneous notes; (2) a graphical display of ECG waveforms time stamped at various decision points, such as verification of an acceptable surface ECG waveforms, advance ECG waveforms, pull back ECG waveforms, and a stop at target ECG waveforms; and (3) a post procedure questionnaire assessing the procedure, the patient, and any other relevant factors. The record could be saved electronically, printed out, or sent transmitted wirelessly to a local or remote server or database.

Figure 9A:
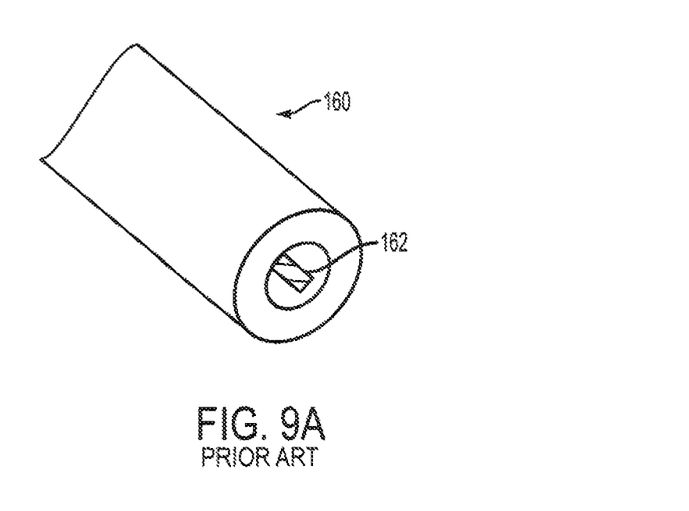
FIG. 9A is prior art figures showing a perspective view of a conventional catheter coaxially surrounding a stylet.

As mentioned above, tip location systems often use a stylet to track changes in the P-wave as the stylet advances towards the SA node. The stylet may be similar to a conventional guidewire, or it could be a specialty stylet with a plurality of electrodes, such as bipolar electrodes disposed at different locations along the stylet. This invention is conceived be used with catheters having a single or multiple lumens. For example, it is possible to have the stylet inserted into a single, double, or triple lumen PICC for placement and removed for subsequent treatment. Alternatively, it may be possible to have a multiple lumen PICC with a dedicated stylet lumen for placement. As shown in prior art FIG. 9A, the distal tip of a catheter 160 can have a stylet 162 positioned at or near the distal opening for acquiring an IV ECG signal. The stylet 162 acts as an electrode and transmits the physiological ECG signal propogated from the SA node from the catheter tip to a proximal connection element such as an alligator clip. The alligator clip is operably connected to the tip location system for signal processing and interpretation of the IV ECG signal.

What is claimed is:
1. A method comprising the steps of:
    acquiring a plurality of surface ECG signals from at least one surface ECG electrode and a plurality of intravascular ECG signals from an intravascular ECG electrode, the intravascular ECG electrode configured to be coaxially surrounded by a peripherally inserted catheter, the at least one surface ECG electrode and the intravascular ECG electrode configured to be connected to a central processing unit (CPU);
    generating an averaged surface ECG signal from the plurality of surface ECG signals and an averaged intravascular ECG signal from the plurality of intravascular ECG signals;
    determining a first fiducial point by identifying a first extremum within the averaged surface ECG signal;
    establishing a first ECG search window between a first predetermined value and a second predetermined value, both the first predetermined value and the second predetermined value being offset from the first fiducial point;
    determining a second fiducial point by identifying a second extremum within the first ECG search window;
    establishing a second ECG search window by identifying a first local extremum on a first side of the second fiducial point and a second local extremum on a second side of the second fiducial point;

applying the second ECG search window to the averaged intravascular ECG signal to generate an intravascular ECG search window;

moving the intravascular ECG electrode from a first location to a second location; and displaying on a display in communication with the CPU, a graphical instruction to a user to advance or retract the intravascular ECG electrode, the graphical instruction to the user to advance or retract the intravascular ECG electrode is in response to the user moving the intravascular ECG electrode from the first location to the second location.

2. The method of claim 1, wherein the averaged intravascular ECG signal is measured over at least five heartbeats.

3. The method of claim 1, wherein the first predetermined value is at least 40 ms prior to the first fiducial point; and the second predetermined value is at least 220 ms prior to the first fiducial point.

4. The method of claim 1, wherein the averaged surface ECG signal is measured over at least five heartbeats.

5. The method of claim 1, wherein the at least one surface ECG electrode is at least two surface ECG electrodes.

6. The method of claim 5, wherein at least two surface ECG electrodes is at least three surface ECG electrodes.

7. A method comprising the steps of:

acquiring a plurality of surface ECG signals from at least one surface ECG electrode and a plurality of intravascular ECG signals from an intravascular ECG electrode, the intravascular ECG electrode configured to be coaxially surrounded by a catheter tip, the at least one surface ECG electrode and the intravascular ECG electrode being connected to a central processing unit (CPU);

generating an averaged surface ECG signal from the plurality of surface ECG signals and an averaged intravascular ECG signal from the plurality of intravascular ECG signals;

determining a first fiducial point by identifying a first extremum, the first extremum identified within the averaged surface ECG signal;

establishing a first ECG search window between a first predetermined value and a second predetermined value, both the first predetermined value and the second predetermined value being offset from the first fiducial point;

determining a second fiducial point by identifying a second extremum, the second extremum identified within the first ECG search window;

establishing a second ECG search window between a first local extremum on a first side of the second fiducial point and a second local extremum on a second side of the second fiducial point so that the second ECG search window is narrower than the first ECG search window;

applying the second ECG search window to the averaged intravascular ECG signal to generate an intravascular ECG search window;

moving the intravascular ECG electrode from a first location to a second location;

displaying, on a display in communication with the CPU, a graphical instruction to a user to advance or retract the intravascular ECG electrode, the graphical instruction to the user to advance or retract the intravascular ECG electrode is in response to the user moving the intravascular ECG electrode from the first location to the second location.

8. The method of claim 7, wherein the averaged intravascular ECG signal is measured over a plurality of at least five heartbeats.

9. The method of claim 7, wherein generating the intravascular ECG search window comprises identifying a fifth extremum, the fifth extremum identified within the averaged intravascular ECG signal.

10. The method of claim 7, wherein the intravascular ECG signal within the intravascular ECG search window is a P-wave.

11. A method comprising the steps of:

acquiring a plurality of surface ECG signals from at least one surface ECG electrode and a plurality of intravascular ECG signals from an intravascular ECG electrode, the at least one surface ECG electrode and the intravascular ECG electrode being connected to a central processing unit (CPU);

generating an averaged surface ECG signal from the plurality of surface ECG signals and an averaged intravascular ECG signal from the plurality of intravascular ECG signals, both the averaged surface ECG signal and the averaged intravascular ECG signal measured over at least 5 heartbeats;

determining a first fiducial point by identifying a first extremum within the averaged surface ECG signal and the averaged intravascular ECG signal;

establishing a first ECG search window between a first predetermined value and a second predetermined value, the first predetermined value and the second predetermined value being offset from the first fiducial point;

determining a second fiducial point by identifying a second extremum within the first ECG search window;

establishing a second ECG search window between a first local extremum on a first side of the second fiducial point and a second local extremum on a second side of the second fiducial point;

applying the second ECG search window to the averaged intravascular ECG signal to generate an intravascular ECG search window;

moving the intravascular ECG electrode from a first location to a second location;

displaying, on a display in communication with the CPU, a graphical instruction to a user to advance or retract the intravascular ECG electrode such that the intravascular ECG electrode is placed at the lower one-third of the superior vena cava (SVC), the graphical instruction is in response to the user moving the intravascular ECG electrode from the first location to the second location.

12. The method of claim 7, further comprising the step of generating a moving averaged intravascular ECG signal.

13. The method of claim 12, further comprising the steps of:

determining a first amplitude based on a third extremum, the third extremum identified within the moving averaged intravascular ECG signal with the intravascular electrode at the first position, and determining a second amplitude based on a fourth extremum, the fourth extremum identified within the moving averaged intravascular ECG signal with the intravascular electrode at the second position.

14. The method of claim 13, wherein:

when the second amplitude is greater than the first amplitude, the graphical instruction to the user to advance the intravascular ECG electrode is displayed.

15. The method of claim 14, wherein the first amplitude and the second amplitude are determined from the moving averaged intravascular ECG signal.

16. The method of claim 13, wherein:
when the second amplitude is less than the first amplitude, the graphical instruction to retract the intravascular ECG catheter is displayed.

* * * * *